United States Patent [19]

Leake

[11] Patent Number: 4,976,737

[45] Date of Patent: Dec. 11, 1990

[54] BONE RECONSTRUCTION

[75] Inventor: Donald Leake, Rolling Hills, Calif.

[73] Assignee: Research and Education Institute, Inc., Torrance, Calif.

[21] Appl. No.: 493,206

[22] Filed: Mar. 14, 1990

Related U.S. Application Data

[63] Continuation of Ser. No. 144,964, Jan. 19, 1988, abandoned.

[51] Int. Cl.$^5$ .............................................. A61B 17/56
[52] U.S. Cl. ...................................... 623/16; 606/60; 606/76
[58] Field of Search ...................... 606/60, 69, 72, 76, 606/77; 623/10, 16; 128/92 V, 92 YQ, 92 YG, 92 YR, 92 YN

[56] References Cited

U.S. PATENT DOCUMENTS

| | | | |
|---|---|---|---|
| 3,849,805 | 11/1974 | Leake et al. | 623/16 |
| 4,436,684 | 3/1984 | White | 623/10 |
| 4,636,215 | 1/1987 | Schwartz | 606/76 |

Primary Examiner—Robert A. Hafer
Assistant Examiner—Kevin G. Rooney

[57] ABSTRACT

A method of forming a surgical mesh material to be used in conjunction with donor bone in reconstructive surgery. A first corporeal model is made of the defect in the bone using computer tomographic techniques. The computer drives a sculpting tool. A second corporeal model is made of missing bone. Surgical mesh is shaped using the second corporeal model as a template. The shaped surgical mesh can be implanted in the patient.

9 Claims, No Drawings

BONE RECONSTRUCTION

This application is a continuation of application Ser. No. 144,964, filed 1/19/88 now abandoned.

This invention relates to surgical methods, particularly surgical methods to reconstruct damaged bone.

A variety of injuries and ailments give rise to skeletal defects. Among them are automobile accidents, gunshot wounds, and various tumors and cancer The defects can be life-threatening. Defects to the skull, particularly the face, even those that would not normally be life-threatening, can be psychologically devastating because of the suddenly changed appearance of the patient.

Advances have been made in surgical technique and diagnosis. Since the widespread adoption of X-ray computer tomography (CT), it has become possible to make three-dimensional projections of bone for preoperative study. White, in U.S. Pat. No. 4,436,684, has adopted CT technology to allow construction of three-dimensional models of a skeletal defect. In many cases, the bilateral symmetry of the skull can be relied on to provide the computer with information about the undamaged half of the skull. The mirror image can be generated, and a model of the missing section of the bone made.

However, even using CT technology, the surgeon must still use shaped bone as the preferred reconstructive material during surgery It is known that dacron/-polyurthane mesh can be used as a surgical insert LEAKE, in U.S. Pat. No. 3,849,805, describes the use of such mesh as a tray to hold bone chips in place for reconstructing damaged or missing mandibular bones.

Conventionally the size and shape of the deformity is estimated by external palpating of the skin over the deformity. Then a cast, made from dental plaster or the like, is made of the portion of the affected anatomy. Since the cast is made from the feel of the injury from the outer skin, the estimation of the size of the defect is always subject to error. Any error made in the modeling of the cast may result in visible bumps or depressions when the surgery heals.

In the procedure of the invention, a three-dimensional model is made from the data gathered during CT scanning. The model, which is a precise representation of the bone, is then used to fashion a prosthesis. Since the X-ray data provides information on the density of the bone, the prosthesis can be made to correct bone damage in diseased bone that feels correct from the surface.

An advantage of a shaped mesh prosthesis is that an object that has been precisely shaped is inserted into the defect with the less precisely shaped donor bone.

It would be advantageous if the shaping technology described by White could be used to form the mesh described by Leake for use as a surgical insert

SUMMARY OF THE INVENTION

An aspect of this invention is a method of reconstructing damaged skeletal features comprising:
fabricating a first three-dimensional corporeal model of the damaged section of the skeleton;
fabricating a second three-dimensional corporeal model of a replacement part for the bone to be replaced of the damaged section of the skeleton; and
forming a surgical mesh material using the second three-dimensional corporeal model as a template.

DETAILED DESCRIPTION OF THE INVENTION

A person's face is one of the most individual and unique things about that person. The appearance of the face is critically dependent on the underlying bone structure. If the facial bone structure is damaged, the outward appearance of the face is changed. Facial appearance is important to the psychological well-being of the patient. Therefore, it is preferable to avoid replacement of damaged facial bone with mass produced prosthesis of the type used for knee or hip reconstruction Herein, a person with an undefined visible skeletal defect will be referred to as "the patient".

Ideally, a facial implant would be modeled on the shape of the pre-diseased bone. This is usually impossible. Fortunately, human faces are nearly bilaterally symmetric. This usually provides a non-diseased, but mirror image, structure that can be used as a model.

There are instances where a mirror image will be difficult or impossible to obtain. An example is a cranial defect in the middle of the forehead In that case, the three-dimensional picture is displayed, and the reconstruction is drawn, using computer graphics, to be as natural looking as possible Although the drawn surface may not be identical with the original surface, it will be better than what could be achieved by the conventional practice of modeling from the outside.

Radiant energy is aimed at the patient's body and used to create a three dimensional computer tomograph. Radiant energy useful in this invention includes x-ray, ultra sound, magnetic resonance, and the like. The three-dimensional computer tomographic image of the damaged skeletal feature, for example, patient's skull is acquired by conventional techniques, usually by use of x-rays The image of the skull can be divided into two bilateral halves. Images useful in this invention will typically have a "normal" or undamaged half and a damaged half.

By standard computer manipulation, as described in U.S. Pat. No. 4,436,684, an image of the skull can be made to be its own mirror image The normal half of the image combined with the mirror image of the normal half yielding a "normal" image of the skull. A skull built to the specifications of this hypothetical "normal" skull would have the advantage that a patient's face, would look natural, and be cosmetically correct The information that makes the mirror image side of the skull is then used to guide an external sculpting tool such as a lathe or milling machine The sculpting tool cuts three-dimensional templates out of wood or plastic or other suitable material. The preferred material is acrylic. A model can be made from wax, and then a more durable model can easily be made with conventional and well-known lost wax techniques. The models created are of two types. A first corporeal model is made showing the surrounding bone as it then exists in the patient This first corporeal model informs the surgeon of what to expect to see when the patient is in surgery. A second corporeal model is then made. It is the model of the missing damaged bone. The second corporeal model is normally a solid accurate representation of the mirror image of the "normal" side of the skull.

The surgical mesh material can be accurately molded using the second three-dimensional corporeal model of the damaged area as a template The molded mesh can then be surgically implanted into the patient The implanted mesh acts as a template for bone used as reconstruction material The preferred surgical mesh material is Dacron/polyurethane. However, any plastic that can be formed by a mold and tolerated when surgically implanted is acceptable in this invention.

The advantage of this procedure is that an accurately shaped mesh can be formed before the surgery. Since the mesh allows healing of bone, the replacement is, after healing, bone Other methods would replace the diseased tissue with an artificial material The risk of rejection or other compatibility problems with the host are thereby substantially reduced by the use of this invention.

In the surgical procedures necessary for the invention, it is usually necessary to provide donor bone of some type. The donor bone is used to graft onto the remaining bone around the skeletal defect thereby forming replacement bone The actual structural components of the healed bone is, therefore, usually bone. Donor bone is typically the patient's ribs, which are usually split, or cancellus bone, usually harvested from the patient's pelvis.

The donor bone is placed at the site of the deformity, and the mesh prosthesis is placed over it. The mesh is normally used to provide the smooth outer surfaces of the replacement. The formed surgical mesh is placed over the donor bone and under the tissue that would normally contact the bone. Then, for example, if split ribs have been used as a donor bone in a cranial reconstruction, the parallel bumpy ridges characteristic of the operation are smoothed by the formed surgical mesh.

The template will have about the same fidelity to the shape of underlying skull as the CT image has. Modern CT scans typically have resolutions of about 1 mm. It is important that the template have as high resolution as possible. The mesh will incorporate template defects when it is formed. If they are large enough, they will be visible after implantation in the patient.

The shaped mesh material provides the structural support for the healing bone Usually the mesh supports only one side of the reconstruction, usually the skin side; that is, it is not a sandwich However, in some cases, for example, in reconstructing the orbits of the eye, the exact shape of the back surface of the bone is as important as the visible surface. Then two layers of mesh material are made that conform with the surfaces to be replaced, and a sandwich of mesh: replacement bone chips: mesh is formed.

The mesh serves a dual purpose It provides the framework that supports the replacement bone, particularly bone chips, in a given three-dimensional shape. It also provides the supporting structure needed during the healing process. Stress placed on the healing wound can deform the shape of the healed replacement bone into an unnatural shape if the stress is not relieved The surgical mesh material relieves the stress.

Of course, in reconstructing the facial bones, the mesh is very important to achieve a cosmetically acceptable result. The complex shapes of the cheeks and eye regions of the face cannot be duplicated by merely replacing the damaged bone structure. The chips must be secured for healing to occur in the selected shape.

It is possible, in the use of this invention, to use the mesh without surgically inserting it. If the defect is, for example, a missing zygomatic arch, the replacement bone, which would probably be a split rib, would have to be shaped at the operating table A surgical mesh material that had been previously shaped can be used as a template for a rib, allowing precise shaping of the rib. The replacement is then surgically implanted without the mesh. In this manner, the unaffected normal side indirectly acts as the template for shaping the replacement bone for the missing arch. Of course, precise shaping of the replacement arch is necessary for a natural-looking healed face.

The underlying bone is covered by the mesh material. Therefore, the replacement bone contours do not have to be cosmetically perfect since the outer facial contours, as seen on the healed patient, will be formed by the mesh material.

In some instances, the properly shaped mesh can be used as a prothesis without donor bone For example, in the orbit of the eye, particularly the orbit floor, the bones are extremely thin. Therefore, rather than replace the bone with rib or pelvic bone, the shaped mesh is placed on the defect in the orbit. The tissue that invades the mesh forms a firm enough platform to function as eye support.

The mesh is preferably made by soaking Dacron in polyurethane. The mesh is then calendared. The Dacron is then tightly attached to the mold, making sure the fit is tight and wrinkle-free. The cloth-covered mold is then baked in an oven at between 65° C. and 120° C. preferably between 90° C. and 95° C. for between 4 hours to 8 hours preferably about 6 hours. The baked mold is then removed from the oven and cured at room temperature for two to four days. Then the mesh freed from the mold. Excess mesh is then cut from the molded mesh. After sterilization, the mesh is packaged for later use or can be implanted in a patient It should be noted that the tray need not necessarily be made from Dacron mesh. Any other material having the physical strength, optimal rigidity, histocompatability, and inertness can be used instead.

I claim:

1. A method of reconstructing damaged facial skeletal features having a pre-damaged shape surrounded, at least in part, by undamaged bone, in a particular patient comprising:
    first, fabricating a first three-dimensional corporeal model of the surrounding portion of undamaged bone of a particular patient's facial skeleton feature;
    second, fabricating a second three-dimensional corporeal model of that section of the facial skeletal feature having the shape of the particular patient's predamaged bone;
    third, forming surgical mesh material having the shape of the particular patient's pre-damaged skeletal features and joining the patient's undamaged facial skeletal features using the joined first and second three-dimensional corporeal models as template for the surgical mesh material thereby forming a customized surgical implant for the patient;
    fourth, placing donor bone at the site of the facial damaged skeletal feature; and
    fifth, securing the customized surgical implant over the donor bone, and between the donor bone and the patient's skin, thereby providing custom shaped structural support for the donor bone lying between the donor bone and the patient's skin, and achieving a cosmetically acceptable replacement of the damaged facial skeletal feature using donor bone.

2. The method of claim 1, including surgically implanting the formed surgical mesh material into the patient.

3. The method of claim 2, including placing the formed surgical mesh over donor bone and under the tissue that normally would contact that bone.

4. The method of claim 1, wherein the second corporeal model is made by forming a mirror image projection of the undamaged half of the skeleton.

5. The method of claim 1, wherein the second corporeal model is made by using the computer projection as a guide for making the best fit.

6. The method of claim 1, wherein said surgical mesh material is dacron/polyurethane mesh.

7. The method of claim 6, wherein said dacron/polyurethane mesh is formed by:
   soaking a piece of unformed dacron mesh in polyurethane;
   calendaring the formed mesh;
   attaching the soaked piece of polyurethane mesh to the second corporeal model;
   baking the mold in an oven at between 65° C. and 120° C. for between four hours to 8 hours;
   curing the baked mesh for two to four days,
   removing the formed mesh from the mold;
   sterilizing and packaging the formed mesh for use in surgery.

8. The method of claim 1, wherein said first three-dimensional corporeal model is made by:
   collecting a data set from radiant energy aimed at the patient's body;
   forming a computer projection of a three-dimensional image of the damaged skeletal feature; and
   using the computer projection to drive an external sculpting tool.

9. A method of reconstructing damaged eye orbits surrounded, at least in part, by undamaged bone, in a particular patient comprising:
   first, fabricating a first three dimensional corporeal model of the surrounding undamaged bone surrounding a damaged portion of a particular patient's eye orbit;
   second, fabricating a second three dimensional corporeal model of the damaged portion of the eye orbit, the second model having the shape of the particular patient's pre-damaged eye orbit;
   third, forming a first surgical mesh material having the shape of the back surface of the eye orbit or the particular patient's pre-damaged bone using the second three-dimensional corporeal model as a template;
   fourth, forming a second surgical mesh material having the shape of the visible contour of the patient's pre-damaged bone using the second three dimensional corporeal model as a template;
   fifth, securing the first surgical mesh at the site of the damaged eye orbit;
   sixth, placing donor bone over the first surgical mesh; and
   seventh, securing the second surgical mesh over the donor bone.

* * * * *